(12) United States Patent
Su et al.

(10) Patent No.: US 9,566,336 B2
(45) Date of Patent: Feb. 14, 2017

(54) IN SITU GELLING DRUG DELIVERY SYSTEM

(71) Applicant: pSivida US, Inc., Watertown, MA (US)

(72) Inventors: Dongling Su, Franklin, MA (US); Paul Ashton, Newton, MA (US); Jianbing Chen, Wayland, MA (US)

(73) Assignee: pSivida US, Inc., Watertown, MA (US)

( * ) Notice: Subject to any disclaimer, the term of this patent is extended or adjusted under 35 U.S.C. 154(b) by 0 days.

(21) Appl. No.: 14/444,338

(22) Filed: Jul. 28, 2014

(65) Prior Publication Data

US 2014/0336278 A1    Nov. 13, 2014

Related U.S. Application Data

(60) Division of application No. 13/612,076, filed on Sep. 12, 2012, now abandoned, which is a continuation of
(Continued)

(51) Int. Cl.
*A61K 9/00* (2006.01)
*A61K 9/06* (2006.01)
(Continued)

(52) U.S. Cl.
CPC ............ *A61K 47/34* (2013.01); *A61K 9/0024* (2013.01); *A61K 9/0051* (2013.01);
(Continued)

(58) Field of Classification Search
CPC .. A61K 31/196; A61K 31/382; A61K 31/485; A61K 31/542; A61K 47/34; A61K 47/481; A61K 47/48215; A61K 47/48784; A61K 9/0024; A61K 9/0051; A61K 9/0092; A61K 9/06
See application file for complete search history.

(56) References Cited

U.S. PATENT DOCUMENTS 4,160,020 A    7/1979 Ayer et al.
5,034,229 A    7/1991 Magruder et al.
(Continued)

FOREIGN PATENT DOCUMENTS

CA    2283939 A1    9/1998
CA    2394716 A1    7/2001
(Continued)

OTHER PUBLICATIONS

Editions Du Vidal Ed.—Editions Du Vidal: "Vidal 1997", Dictionnaire Vidal 1997, Paris, Editions Du Vidal, Fr, Neoral, XP002334163.
(Continued)

*Primary Examiner* — Aradhana Sasan
(74) *Attorney, Agent, or Firm* — Foley Haug LLP; David P. Halstead (57) ABSTRACT

The invention provides liquid controlled-release drug delivery compositions which gel upon injection into the body to form, in situ, controlled-release drug implants. The compositions of the invention feature a gel-forming polymer that is insoluble in water, a polyethylene glycol solvent in which the polymer is dissolved, and the drug substance to be delivered.

10 Claims, 4 Drawing Sheets

Related U.S. Application Data application No. 12/870,616, filed on Aug. 27, 2010, now abandoned, which is a continuation of application No. 10/877,758, filed on Jun. 25, 2004, now abandoned.

(60) Provisional application No. 60/482,677, filed on Jun. 26, 2003, provisional application No. 60/575,307, filed on May 28, 2004.

(51) Int. Cl.
*A61K 31/196* (2006.01)
*A61K 31/382* (2006.01)
*A61K 31/485* (2006.01)
*A61K 31/542* (2006.01)
*A61K 47/34* (2006.01)
*A61K 47/48* (2006.01)

(52) U.S. Cl.
CPC .............. *A61K 9/0092* (2013.01); *A61K 9/06* (2013.01); *A61K 31/196* (2013.01); *A61K 31/382* (2013.01); *A61K 31/485* (2013.01); *A61K 31/542* (2013.01); *A61K 47/481* (2013.01); *A61K 47/48215* (2013.01); *A61K 47/48784* (2013.01)

(56) References Cited

U.S. PATENT DOCUMENTS

| | | | |
|---|---|---|---|
| 5,057,318 A | 10/1991 | Magruder et al. | |
| 5,110,596 A | 5/1992 | Magruder et al. | |
| 5,324,280 A | 6/1994 | Wong et al. | |
| 5,324,519 A | 6/1994 | Dunn et al. | |
| 5,378,475 A | 1/1995 | Smith et al. | |
| 5,516,527 A | 5/1996 | Curatolo | |
| 5,618,560 A | 4/1997 | Bar-Shalom et al. | |
| 5,681,964 A | 10/1997 | Ashton et al. | |
| 5,736,152 A | 4/1998 | Dunn | |
| 5,744,153 A | 4/1998 | Yewey et al. | |
| 6,102,887 A * | 8/2000 | Altman | A61M 25/0084 604/22 |
| 6,156,764 A | 12/2000 | Asmussen et al. | |
| 6,375,972 B1 | 4/2002 | Guo et al. | |
| 2002/0173586 A1* | 11/2002 | Jeong et al. | 524/599 |
| 2003/0082234 A1 | 5/2003 | Seo et al. | |
| 2004/0176341 A1* | 9/2004 | Chou | A61K 9/0004 514/179 |
| 2006/0078618 A1 | 4/2006 | Constantinides et al. | |

FOREIGN PATENT DOCUMENTS

| | | |
|---|---|---|
| CA | 2473526 A1 | 7/2003 |
| JP | S59-110607 | 6/1984 |
| JP | 2229110 | 9/1990 |
| JP | 5305135 B2 | 10/2013 |
| WO | WO-95/30410 A2 | 11/1995 |
| WO | WO-96/40049 A1 | 12/1996 |
| WO | WO-97/26015 A1 | 7/1997 |
| WO | WO-98/27962 A2 | 7/1998 |
| WO | WO-98/27963 A2 | 7/1998 |
| WO | WO-00/35419 A2 | 6/2000 |
| WO | WO-00/74650 A2 | 12/2000 |
| WO | WO-02/00137 A1 | 1/2002 |
| WO | WO-02/36169 A2 | 5/2002 |
| WO | WO-02/45689 A1 | 6/2002 |
| WO | WO-02/49573 A2 | 6/2002 |

OTHER PUBLICATIONS

Jain, R.A., et al; "Controlled delivery of drugs from a novel injectable in situ formed biodegradable PLGA microsphere system"; Journal of Microencapsulation, Taylor and Francis Inc., London, GB; vol. 17, No. 3, May 2000; pp. 343-362; XP-000912452; ISSN: 0265-2048.

Novartis: "Neoral" Internet Article, [Online] XP002334091 Retrieved from the Internet: URL:http://www.pharma.us.novartis.com/product/pi/pdf/neoral.pdf>[retrived on Jun. 29, 2005].

International Search Report and Written Opinion for PCT/US2004/020369 dated Jan. 17, 2005.

International Search Report and Written Opinion for PCT/US2004/020547 dated Jul. 19, 2005.

ROC (Taiwan) Search Report for Application No. 093118702 dated Mar. 3, 2010.

* cited by examiner

IN SITU GELLING DRUG DELIVERY SYSTEM

RELATED APPLICATIONS

This application is a divisional of U.S. patent application Ser. No. 13/612,076, filed Sep. 12, 2012 (now abandoned), which is a continuation of U.S. patent application Ser. No. 12/870,616, filed Aug. 27, 2010 now abandoned), which is a continuation of U.S. patent application Ser. No. 10/877,758, filed Jun. 25, 2004 (now abandoned), which claims the benefit of U.S. Provisional Application No. 60/482,677, filed Jun. 26, 2003, and U.S. Provisional Application No. 60/575,307, filed May 28, 2004, the specifications of which are incorporated by reference herein in their entirety.

FIELD OF THE INVENTION

The present invention relates to the field of controlled-release and sustained-release drug delivery systems, and particularly to the field of injectable drug delivery implants.

BACKGROUND OF THE INVENTION

There are many useful drugs on the market today for which traditional means of administration are far from ideal. Bolus injections and oral unit doses typically result in a high initial systemic concentration of the active agent, in excess of the therapeutic concentration, which falls off over time and which will fall below the therapeutic concentration if another bolus is not timely administered. The result is that the ideal therapeutic concentration is not consistently maintained, there is a risk of toxicity associated with high systemic exposure to the drug, and the maintenance of a minimally effective concentration is dependent upon repeated administration at prescribed intervals. Patient compliance with a dosing regimen is difficult to ensure, especially where the course of therapy is long or of indeterminate or lifetime duration. There is a need for methods to deliver these drugs more effectively, so that therapeutic concentrations are maintained constantly in the tissues intended to be treated over an extended period of time, with minimal vulnerability to the vagaries of patient compliance, and ideally with minimal systemic exposure or exposure of uninvolved tissues and organs.

Modern drug discovery methods have led to the development of many drugs which are far more potent, yet have poorer solubility, than drugs developed through traditional medicinal chemistry methods. The development of these often-complex drugs has resulted in a need for methods to deliver such drugs more effectively and efficiently as well.

Extended-release and controlled-release drug delivery systems have been developed to address these needs. Implanted pumps and reservoirs, with various mechanisms for regulating release of drugs, were among the first solutions to be developed. A wide variety of polymeric matrices, permeated with drug substance, have also been developed which serve as implantable drug reservoirs. These polymeric implants gradually release drug over the course of days, weeks, or months as the contained drug diffuses through and out of the matrix and into the surrounding tissue. Three principal advantages provided by polymeric drug delivery compositions are:

(1) Localized delivery of drug. The product can be implanted directly at the site where drug action is needed and hence systemic exposure of the drug can be reduced. This becomes especially important for toxic drugs which are related to various systemic side effects (such as the chemotherapeutic drugs).

(2) Sustained delivery of drug. The drug is released over extended periods, eliminating the need for multiple injections or oral doses. This improves patient compliance, especially for drugs for chronic indications requiring frequent administration, such as replacement therapy for enzyme or hormone deficiencies, or for extended antibiotic treatments for such tenacious diseases as tuberculosis.

(3) Stabilization of the drug. The polymer matrix protects the drug from the physiological environment, particularly circulating enzymes, thereby improving stability in vivo. This makes the technology particularly attractive for the delivery of labile proteins and peptides.

For the reasons above, the use of drug-infused polymer implants as sustained-release drug delivery devices is now well established. One class of existing implants consists of preformed devices, ranging in size from matchstick-sized cylindrical rods such as the Norplant™ (levonorgestrel) and Zoladex™ (goserelin acetate) implants, to microspheres such as are sold under the trade name Lupron Depot™ (leuprolide acetate).

A major disadvantage of the macroscopic devices is their physical size. Implantation of Zoladex™ rods, for instance, requires the use of 14- or 16-gauge needles, and implantation of Norplant™ rods requires a surgical incision under local anesthesia, with similar subsequent procedures to replace and/or remove them. (The Zoladex™ rods are bioerodable, whereas Norplant™ implants are based on a non-bioerodable silicone.) Self-administration of such implants is not feasible, and the required intervention of trained medical personnel greatly raises the cost and inconvenience of such treatments.

Drug-containing polymer implants have been reduced in size by the expedient of grinding or milling a mixture of a drug substance and a gel-forming polymer at low temperature, as described in U.S. Pat. No. 5,385,738. The resulting powder is then suspended in a non-aqueous viscous solvent, such polyethylene glycol or a biocompatible oil, to obtain an injectable composition.

The size problem has similarly been overcome with microsphere implants, which can be administered (and self-administered where appropriate) by injection of an aqueous suspension of the microspheres. Lupron Depot™, for example, can be comfortably injected with a 22- or 23-gauge needle. Because microspheres are not retrievable from the body, they are necessarily based on bioerodable polymers. However, if an aqueous suspension of microspheres is stored for any length of time, the drug will diffuse from the particles into the aqueous phase, furthermore the bioerodable matrix itself is prone to hydrolysis in an aqueous environment. For these reasons, the injectable aqueous suspension must be prepared at the time of injection. A second disadvantage is the need for intramuscular injection. Finally, preparation of the microspheres is a complex process that is not easily carried out reproducibly and reliably, and regulatory validation of the manufacturing process can be a significant obstacle to commercialization of such products.

Another class of implants differing from pre-formed solid devices is injectable liquids. Upon injection, these are transformed in situ into solid implants. This class of implants is typified by compositions that transform from a drug-containing liquid phase to a drug-infused gel phase upon exposure to a physiological environment. Such in situ gelling compositions have several advantages: they can be readily and reliably manufactured by standard methods, they can be stored in the form of easily-injected liquids, they can be placed locally to achieve local delivery, and they can flow prior to gelling so as to fill voids and create a less-visible subcutaneous implant. In addition, a gelling, implant can serve as a scaffold for cellular colonization and tissue growth.

There are various changes in conditions that can trigger the gelling of an in situ gelling composition. Among these are changes in pH, osmolality, temperature, water concentration, and alterations in specific ion concentrations.

Temperature-sensitive in situ gelling compositions generally change from a sol to a gel when the temperature exceeds a critical solution temperature, which in the case of drug delivery systems must be reasonably close to body temperature. An example is the polyethylene oxide-polypropylene oxide block copolymer, sold under the trade name Pluronic™ F 127. A 25-40% aqueous solution of this material will gel at about body temperature, and drug release from such a gel occurs over a period of up to one week. Such compositions have the disadvantage that they must be carefully protected from premature gelling, through refrigerated storage, and no bioerodable polymer has yet been developed that undergoes a sol-gel transition at about body temperature.

A hydrogel whose drug release profile is both temperature- and pH-modulated has also been reported (T. G. Park, in *Biomaterials* 20:517-521 (1999)).

Another class of compositions form gels upon contact with water. For example, glycerol monooleate (GMO) containing a drug can be injected as a liquid lamellar phase, which upon injection and exposure to water forms a highly viscous cubic-phase hydrate. The drug is released from the cubic phase over the course of several days. An example of an injectable drug depot product based on GMO is the metronidazole dental gel formulation marketed under the trade name Elyzol™. Due to the high water content of the cubic phase, GMO formulations are prone to rapid drug release and are limited in duration of effect to no more than about five days.

There are very few biocompatible liquid crystal compositions that meet the requirement for phase transition to a sufficiently viscous state at physiological conditions. Polymers that precipitate upon contact with water, on the other hand, are numerous, and present a more versatile approach to the formulation of compositions that gel upon contact with water. Approaches based on in situ gelling compositions are described in U.S. Pat. Nos. 4,938,763, 5,077,049, 5,278,202, 5,324,519 and 5,780,044, all of which are incorporated herein by reference.

For example, the Atrigel™ drug delivery system consists of a bioerodable poly(DL-lactide-glycolide) (PLGA) copolymer (75:25 molar ratio) dissolved in N-methyl-2-pyrrolidone (NMP). Pharmaceuticals may be blended into this PLGA solution at the point of manufacture, or they may be added by the physician at the time of use. The liquid product is injected subcutaneously or intramuscularly through a small gauge needle, whereupon displacement of the NMP carrier with water in the tissue fluids causes the PLGA to precipitate, forming a solid film or implant. The drug incorporated within the implant is then released in a controlled manner as the polymer matrix erodes with time in the body. PLGA-based implants of this type can release drug over a period of several months. An example of a product employing this technology is the leuprolide acetate formulation marketed under the trade name Eligard™.

The Atrigel™ system uses N-methylpyrrolidinone (NMP) as a solvent for the PLGA copolymer. NMP is a water-miscible, low-molecular-weight and low-viscosity solvent that rapidly diffuses from the implant. Rapid solvent escape from the injected composition can lead to rapid and uneven precipitation of the polymer, shrinking of the implant, and local irritation or even necrosis due to exposure of tissues to a high local concentration of solvent.

The use of liquid polymers as solvents for in situ gel-forming compositions has been described in U.S. Pat. No. 5,607,686 and in U.S. application Ser. No. 10/169,012 (US 2003/0082234), corresponding to international patent application PCT/KR00/01508 (WO 01/45742). However, according to these patents, polyethylene glycol is not suitable as a solvent for PLGA.

In situ polymer-precipitation systems solve many of the problems associated with implants, but some difficulties remain. There is a need for in situ gelling drug delivery systems with improved properties, a simple preparation procedure and low toxicity of excipient.

PEGs have the advantage of solubilizing different drugs than NMP; in particular pegylated proteins can be expected to be more soluble and/or miscible in PEGs than in NMP. An additional advantage is that PEGs are available in different molecular weights and have different viscosities. In many instances it important to be able to control the viscosity of the injected gelling agent, which is not possible with NMP.

BRIEF DESCRIPTION OF THE INVENTION

The morphology of the polymer gel produced during the precipitation process is dependent upon the nature of the organic solvent, which can vary from a dense sponge-like structure to an open meshwork with numerous voids and channels (P. D. Graham et al., *J. Controlled Release* 58:233-245 (1999)). This morphology in turn affects both the initial burst and the sustained release kinetics of the gel. Solvents used to date for this purpose have largely been selected from the chemist's traditional menu of low-molecular weight species, such as NMP, DMA, alcohols, and the like, as described for example in U.S. Pat. No. 5,780,044.

Applicants have found that polyethylene glycol can serve as the solvent for PLGA, and have found that the gel phase produced upon exchange of the PEG with water exhibits desirable sustained-release kinetics for small-molecule drugs.

Accordingly, the present invention provides an in situ gelling drug delivery formulation comprising a drug substance and a PLGA polymer, dissolved dispersed or suspended in PEG as the liquid phase solvent. In certain embodiments, the liquid phase solvent may include, or even consist essentially of, a prodrug of the drug substance combined with PEG. The compositions of the invention, on contact with water or bodily fluids, undergo exchange of the PEG for water, resulting in precipitation of the both the polymer and the drug and subsequent formation of a gel phase within which the drug substance is incorporated. The drug substance subsequently diffuses from the gel over an extended period of time.

The present invention also provides methods for making in situ gelling drug delivery formulations comprising a drug substance and a PLGA polymer, dissolved dispersed or suspended in PEG as the liquid phase solvent. The invention also provides methods for preparing sustained-release drug depots in situ by the use of such formulations.

DETAILED DESCRIPTION OF THE INVENTION

The present invention provides injectable in situ gelling pharmaceutical compositions, comprising: (a) a drug substance; (b) a liquid, semi-solid, or wax polyethylene glycol (PEG); and (c) a biocompatible and bioerodable polymer that is dissolved, dispersed, or suspended in the PEG.

A "liquid" PEG is a polyethylene glycol that is a liquid at 20-30° C. and ambient pressure. In certain preferred embodiments, the average MW of the liquid PEG is between about 200 and about 400. The polyethylene glycol may be linear or it may be a bioabsorbable branched PEG, for example as disclosed in U.S. Patent application No. 2002/0032298. In certain alternative embodiments the PEG may be a semi-solid or wax, in which case the $M_n$ will be larger, for example 3,000 to 6,000. It will be understood that compositions comprising semi-solid and waxy PEGS may not be amenable to injection, and will accordingly be implanted by alternative means.

In certain embodiments, the drug substance is dissolved in the polyethylene glycol, while in other embodiments the drug substance is dispersed or suspended in the PEG in the form of solid particles. In yet other embodiments, the drug substance may be encapsulated or otherwise incorporated into particles, such as microspheres, nanospheres, liposomes, lipospheres, micelles, and the like, or it may be conjugated to a polymeric carrier. Any such particles are preferably less than about 500 microns in diameter, more preferably less than about 150 microns.

The present invention also provides for macroscopic drug delivery devices, for example in the form of hollow particles, capsules or open tubes, which contain an in situ gelling composition of the invention. The devices may be permeable to the drug substance, or they may be impermeable with one or more openings through which the drug substance may exit the device. Such devices, which are well-known in the art, provide additional control over the release rate of the drug substance, by controlling the diffusion rate and/or surface area through which the drug substance is released.

The drug substance in certain embodiments is a peptide or protein, which optionally may be pegylated, while in other embodiments the drug substance is a prodrug or a co-drug. The drug substance may be in the form of a salt, which may be a low-solubility salt. In certain embodiments exemplified herein, the drug substance is the diclofenate ester of morphine.

The compositions of the invention may optionally contain additives, such as pore-forming agents (e.g., sugars, salts, and water-soluble polymers) and release rate modifiers (e.g., sterols, fatty acids, glycerol esters, and the like).

In another aspect, the invention provides a method for administering a drug substance to a subject, which comprises injecting into the subject a composition comprising (a) a drug substance; (b) a liquid PEG; and (c) a biocompatible and bioerodable PLGA polymer that is dissolved in the PEG. As used herein, "subject" refers to both human and animal patients to whom the drug is to be administered.

In yet another aspect, the invention provides a method for forming a polymeric sustained-release drug delivery gel in a subject, which comprises injecting into the subject a composition comprising (a) a drug substance; (b) a liquid PEG; and (c) a biocompatible and bioerodable PLGA polymer that is dissolved in the polyethylene glycol.

The present invention also provides for the co-administration of a PEG/polymer/drug fluid with an aqueous fluid, which may be for example normal saline or a hydrogel. In this embodiment, the two fluids are either administered at the same time via a double lumen needle, or mixed immediately before administration. The two fluids may be in contained in attached syringes. Co-administration reduces the local irritation that may be caused by direct application of highly concentrated PEGs.

The polymer may be any biocompatible PLGA polymer that is soluble in or miscible with PEG, and is less soluble in water. It is preferably water-insoluble, and is preferably a bioerodable polymer. The carboxyl termini of the lactide- and glycolide-containing polymer may optionally be capped, e.g., by esterification, and the hydroxyl termini may optionally be capped, e.g., by etherification or esterification. Preferably the polymer is PLGA having a lactide:glycolide molar ratio of between 20:80 and 90:10, more preferably between 50:50 and 85:15.

Bioerodable polymers are polymers which gradually degrade to smaller chemical fragments when placed in the subject's body. Two types of degradable polymers are included under this definition: biodegradable polymers (whose biodegradation is enzymatically mediated) and bioabsorbable polymers (which degrade to smaller fragments in the presence of water and/or other chemical species in the body). Some bioerodable polymers, e.g., certain block co-polymers, may be subject to both modes of degradation.

Biocompatible polymers are those polymers which, when injected or implanted in the subject's body, do not cause inflammation or irritation, do not induce an immune reaction, and do not exhibit toxicity.

The in situ gelling compositions of the present invention are suitable for delivering small organic molecules as well as peptides, proteins, polysaccharides, and nucleic acids. The drug substance may be a pharmaceutically active substance, a pro-drug that is converted in vivo into a pharmaceutically active substance, or a co-drug that is converted in vivo into two or more pharmaceutically active substances. By co-drug is meant a combination of two or more drugs whose molecules are physically linked, for example by covalent or ionic bonds. Examples of suitable co-drugs are described in U.S. patent application Ser. No. 10/134,033 (publication US 2003/0039689) and U.S. patent application Ser. No. 10/349,202, which are incorporated herein by reference. The drug substance may be soluble or insoluble in PEG. If insoluble, the drug substance is preferably suspended in the PEG in the form of fine particles.

By way of example, and not limitation, drug substances suitable for use in the present invention include physiologically active peptides and/or proteins, antineoplastic agents, antibiotics, analgesics, anti-inflammatory agents, muscle relaxants, anti-epileptics, anti-ulcerative agents, anti-allergic agents, cardiotonics, anti-arrhythmic agents, vasodilators, antihypertensive agents, anti-diabetic agents, anti-hyperlipidemics, anticoagulants, hemolytic agents, antituberculous agents, hormones, narcotic antagonists, osteoclastic suppressants, osteogenic promoters, angiogenesis suppressors, and various mixtures, salts, prodrugs and co-drugs thereof.

Physiologically active peptides and/or proteins range in molecular weight front 200 to 100,000 and include but are not limited to human growth hormone, growth hormone releasing hormone, growth hormone releasing peptide, interferons, colony stimulating factors, interleukins, macrophage activating factors, macrophage peptide, B-cell factors, T-cell factors, protein A, allergy repressors, immunotoxins, lymphotoxins, tumor necrosis factors, tumor repression factors, vascular endothelial growth factor (VEGF), fibroblast growth factor (FGF), metastasis growth factors, alpha-1 antitrypsin, apolipoprotein-E, erythropoietin, Factor VII, Factor VIII, Factor IX, plasminogen activating factors, urokinase, streptokinase, Protein C, C-reactive protein, superoxide dismutase, platelet-derived growth factors, epidermal growth factors, osteogenic growth factors, osteogenesis-promoting proteins, calcitonin, insulin, atriopetin, cartilage induction factors, connective tissue activating factors, follicle stimulating hormone, leutenizing hormone, leutenizing hormone releasing hormone, nerve growth factors, parathyroid hormone, relaxin, secretin, somatomedin, insulin-like growth factors, adrenocorticotropic hormone, glucagons, cholecystokinin, pancreatic polypeptides, gastrin releasing hormone, coticotropin releasing factors, thyroid stimulating hormones, mono- and poly-clonal antibodies, vaccines, and mixtures thereof. Pegylated versions of proteins, peptides, or other biologic response modifiers are also suitable for incorporation into the compositions of the present invention.

Antiproliferative/antimitotic drugs and prodrugs include natural products such as vinca alkaloids (e.g., vinblastine, vincristine, and vinorelbine), paclitaxel, epidipodophyllotoxins (e.g., etoposide, teniposide), antibiotics (e.g., actinomycins, daunorubicin, doxorubicin and idarubicin), anthracyclines, mitoxantrone, bleomycins, plicamycin (mithramycin) and mitomycin, enzymes (e.g., L-asparaginase); antiplatelet prodrugs; antiproliferative/antimitotic alkylating prodrugs such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), triazenes, dacarbazine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine (cladribine); platinum coordination complexes (cisplatin, carboplatin), procarbazine, hydroxyurea, mitotane, aminoglutethimide; hormones (e.g., estrogen, progestin); anticoagulants (e.g., heparin, synthetic heparin salts and other inhibitors of thrombin); fibrinolytic prodrugs such as tissue plasminogen activator, streptokinase and urokinase, aspirin, dipyridamole, ticlopidine, clopidogrel, abciximab; antimigratory; antisecretory (breveldin); anti-inflammatory agents such as corticosteroids (cortisol, cortisone, fludrocortisone, flucinolone, prednisone, prednisolone, methylprednisolone, triamcinolone, betamethasone, and dexamethasone), NSAIDS (salicylic acid and derivatives, aspirin, acetaminophen, indole and indene acetic acids (indomethacin, sulindac and etodalac), heteroaryl acetic acids (tolmetin, diclofenac, and ketorolac), arylpropionic acids (e.g., ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives (e.g., cyclosporine, tacrolimus (FK-506), sirolimus (rapamycin), azathioprine, and mycophenolate mofetil); angiogenic agents such as vascular endothelial growth factor (VEGF), fibroblast growth factor (FGF); angiotensin receptor blocker; nitric oxide donors; anti-sense oligionucleotides and combinations thereof; cell cycle inhibitors, mTOR inhibitors, and growth factor signal transduction kinase inhibitors.

In certain embodiments, the drug substance is a prodrug or co-drug of an opioid analgesic or an opioid antagonist. Exemplary opioids include morphine and morphine derivatives, such as apomorphine, buprenorphine, codeine, dihydrocodeine, dihydroetorphine, diprenorphine, etorphine, hydrocodone, hydromorphone, levorphanol, meperidine, metopon, o-methylnaltrexone, naloxone, naltrexone, normorphine, oxycodone, and oxymorphone. In other embodiments, the opiod is fentanyl or a fentanyl derivative which can be derivatized to form a prodrug or co-drug, such as beta-hydroxy-3-methylfentanyl. The drug substances may optionally be in pharmaceutically acceptable salt forms.

The polyethylene glycol solvent may be a PEG that is liquid at room temperature and ambient pressure, having an average MW of between about 100 and about 600, preferably between about 200 and about 400. Alternatively it may be a semi-solid or wax PEG, having an average molecular weight up to about 6,000. The ratio of polyethylene glycol to polymer will typically range from about 25:1 to about 1:20 by weight.

The compositions of the invention can be used to maintain therapeutically effective systemic levels of suitably potent drugs that have an appropriate elimination rate. The invention can also be used to maintain therapeutically effective localized levels of suitably potent drugs having appropriate clearance rates.

The compositions of the invention may be prepared by stirring PEG, the drug substance, and polymer together until solution is obtained. Dissolution may be accelerated by heating and agitation. Where the drug substance is not soluble in the PEG, the drug substance is preferably provided in the form of a microparticulate or nanoparticulate powder that will form a suspension in the polymer-PEG solution.

In certain embodiments, the drug substance may be covalently linked to a polyoxyethylene ether (e.g., PEG), wherein the covalent bonds are cleavable in vivo so as to release the drug substance. In certain embodiments, the drug substance is released in a sustained manner. Methods shown for forming and applying conjugate prodrugs (e.g., PEG—drug conjugates) are shown in U.S. Pat. No. 5,681,964 and in U.S. Provisional Application No. 60/539,306, the specifications of which are incorporated by reference in their entirety herein.

In certain embodiments, the drug substance is a pegylated prodrug of another drug substance.

In certain embodiments the drug substance may be included in compounds having structure 1 below:

$$A(-L-)_m S_n \qquad \qquad 1$$

wherein A is a residue of a pharmaceutically active agent A', L represents a covalent bond or a linker moiety, and S is a polyoxyethylene ether group having the formula —(OCH$_2$CH$_2$)$_p$OR, where p is 2-12 and R is a C$_1$-C$_4$ alkyl group. The biocompatible fluid may comprise a mixture of compounds having a range of values of p; but in preferred embodiments p has a single value and the composition comprises only one compound of structure 1. The bond or linker L is cleavable in vivo so as to release the active agent A'. The agent A' will typically feature one or more functional groups to which linkers L can be readily attached. Examples of such functional groups include but are not limited to —CO$_2$H, —CONH$_2$, —CHO, =O, —OH, —NH$_2$, and —SH groups.

Examples of bonds and linkages which are cleavable in vivo, either by hydrolysis or by enzyme catalysis, include but are not limited to esters, amities, carbamates, carbonates, orthoesters, cyclic ketals, thioesters, thioamides, thiocarbamates, thiocarbonates, xanthates, disulfides, and phosphate esters. Ester linkages, carbonate linkers, and/or amino acid linker moieties are preferred. Enzymatically cleavable linkers for polyoxyethylene derivatives have been described, for example, in U.S. Pat. No. 6,127,355, Ulbrich et al., *Makromol. Chem.* 1986; 187:1131-1144, Conover et al., and *Anti-Cancer Drug Design* 1999; 14:499-506, and in many of the references cited therein, and the use of such linkers is specifically contemplated. Ester linkages may also be used (see R. Bronaugh et al., *Percutaneous Absorption* 3rd Ed., p. 58-63, R. L. Bronaugh and H. I. Maibach, eds., Marcel Dekker, New York, 1999).

The values of m and n will typically range front 1 to 4, although larger values are within the scope of the invention. Typically, the linker is divalent and m and n will have the same value, but multiple links to a single moiety S, as for example in a ketal or orthoester linkage, may be employed. Alternatively, multiple moieties S may be appended via a single linker L, for example by esterification of the agent A with a moiety such as —C(=O)CH[(OCH$_2$CH$_2$)$_p$OR]$_2$ or —P(=O)[(OCH$_2$CH$_2$)$_p$OR]$_2$. Where m>1 and/or n>1, each incidence of L and S may be the same or different.

The residue represented by A may be derived from any drug substance, including but not limited to steroids (preferably corticosteroids), retinoids, NSAIDs, vitamin D3 and vitamin D3 analogs, antibiotics, and antiviral agents. Other suitable agents include enzymes, peptides and other large molecules. In certain embodiments of this invention, all-trans retinoic acid is excluded from the residues represented by A, while in other embodiments retinoids are excluded from the residues represented by A.

Suitable steroids include but are not limited to androgenic and estrogenic steroid hormones, androgen receptor antagonists and 5-α-reductase inhibitors, and corticosteroids. Specific examples include but are not limited to alclometasone, clobetasol, fluocinolone, fluocortolone, diflucortolone, fluticasone, halcinonide, mometasone, prednisone, prednisolone, methylprednisolone, triamcinolone, betamethasone, and dexamethasone, and various esters and acetonides thereof.

Suitable retinoids include but are not limited to retinol, retinal, isotretinoin, acitretin, adapalene, tazarotene, and bexarotene.

Suitable NSAIDs include but are not limited to naproxen, suprofen, ketoprofen, ibuprofen, flurbiprofen, diclofenac, indomethacin, celecoxib, and rofecoxib.

Suitable vitamin D3 analogues include but are not limited to doxercalciferol, seocalcitol, calcipotriene, tacalcitol, calcitriol, ergocalciferol, and calcifediol.

Suitable antiviral agents include but are not limited to trifluridine, cidofovir, acyclovir, penciclovir, famciclovir, valcyclovir, gancyclovir, and docosanol. Suitable antibacterial agents include but are not limited to metronidazole, clindamycin, erythromycin, vancomycin, ciprofloxacin, ofloxacin, lomefloxacin, bacitracin, neomycin, mupirocin, and polymyxin B. The antiviral and antibacterial prodrugs of the invention may be used to treat appropriately responsive systemic infections.

The linker L is cleavable in vivo, meaning that the compound of the invention is hydrolyzed or otherwise cleaved, with or without enzymatic catalysis, so as to generate in situ the active drug substance.

Examples of suitable linkers include, but are not limited to, —CH$_2$O—, —OCH$_2$O—, —C(=O)—O—, —OC(=O)—O—, —C(=O)—(CH$_2$)$_{1-4}$—O—, and —C(=O)—(CH$_2$)$_{1-4}$—, —C(=O)—NH—, and —C(=S)—NH—. Descriptions of suitable linkers may be found in *Prodrugs: Topical and Ocular Drug Delivery*, 1992, K. B. Sloan (Ed.), Drugs and the Pharmaceutical Sciences, Vol 53 (Marcel Dekker). It will be appreciated that the rate of cleavage will vary depending on the precise structures of the active agent and the polyoxyethylene ether, and on the nature of the linker or bond L and the point(s) of attachment. The efficiency of prodrug cleavage of linkers for any specific embodiment can be readily determined by those of skill in the art; for a review of methods see A. Stichcomb, 2003, *Pharm Res.* 20:1113-1118.

The linker or bond L may be attached to any suitable heteroatom present in the topically active agent that carries an exchangeable hydrogen, such as —OH, SH, NH$_2$, and COOH groups. By way of example, the free hydroxyl group of triamcinolone acetonide may be acylated with the moiety —C(=O)(OCH$_2$CH$_2$)$_p$OR.

In one embodiment, the active drug substance comprises a carboxylic acid group, and the carboxylic acid group is esterified with a polyoxyethylene ether of formula HO(CH$_2$CH$_2$O)$_p$R. Examples include but are not limited to structures I, II, and III shown below:

In an alternative embodiment, the active drug substance comprises a hydroxyl group, and the hydroxyl group is acylated with a polyoxyethylene ether carbonyl moiety of formula —CO(OCH$_2$CH$_2$)$_p$OR. Examples include but are not limited to structures IV and V shown below:

In certain embodiments, the biocompatible fluid includes a prodrug comprising a pharmaceutical compound linked to a polyoxyethylene ether moiety of the formula: —(OCH$_2$CH$_2$)$_p$OR, wherein p=2-12 and R is a C$_1$-C$_4$ alkyl group. In certain embodiments, n is an integer from 2 to 6 inclusive. The identities of the group R may be methyl, ethyl, or any other organic moiety.

In certain embodiments, the use of prodrug linkages in connection with a drug substance may improve the solubility of an agent in water or in polymer. For example, the use of a pegylated prodrug may improve the solubility of an agent in the biocompatible fluid, and thereby improve the injectability of the invention. The use of prodrug linkages may also lower the melting point of a solid drug substance, or increase the solubility of a drug substance in physiological fluids, thereby improving the injectability of the drug substance.

The drug substance may be dissolved, dispersed or suspended in the biocompatible core, whereupon it may leach out of the core and into surrounding fluid. In certain embodiments, the drug substance may rapidly escape from an injection mixture after injection into a physiological system.

The term "residue" when applied to an agent means a part of an agent that is substantially identical to the agent from which it is derived, with minor differences arising by virtue of having one or more atoms removed to provide points of attachment for the linker(s) L. Typically, at least one functional group of the residue will be altered (relative to the parent pharmaceutically active agent) to accommodate the covalent linker. This will typically involve removal of an exchangeable hydrogen and/or a single heteroatom, leaving a free valence for attachment of the linkage L. For instance, where the drug substance includes a carboxylate functional group, the residue of the agent formed by removal of a hydroxyl group may form an ester bond with a hydroxyl group on a polyoxyethylene ether residue, which itself is formed by removal of a hydrogen atom from a hydroxyl group from the polyoxyethylene ether. In this sense, the term "residue" as used herein is analogous to the sense of the word as it is used in peptide and protein chemistry to refer to a residue of an amino acid in a peptide.

The terms "linker" and "linkage," which are used interchangeably herein, refer to a direct bond or to a multivalent group of atoms incorporating and connecting the functional groups of the active drug substance and a polyoxyethylene ether, which is metabolized under physiological conditions to release the active agent A'. In certain embodiments, the linker is a substantially linear moiety having no more than 25 atoms, more preferably less than 10 atoms. Preferred linkers are ones which, upon release of the topically active agent, and when further metabolized, generate byproducts that are non-toxic and inert at the effective dosing concentration. Direct bonds between the residue A and the polyoxyethylene moiety S are particularly preferred.

EXAMPLES

Example 1

Evaluation of Solubility of PLGA in Organic Solvents

A sample of PLGA polymer was added to the indicated solvent and overnight at room temperature, and the resulting mixture was examined for undissolved material. The results are shown in Table 1 below.

TABLE 1

Solubility of PLGA polymers in selected organic solvents

| Polymer | Solvent | Visual Appearance |
| --- | --- | --- |
| PLGA (70:30), 0.2 g | PEG 400, 1 ml | Clear solution |
| PLGA (70:30), 0.2 g | PEG 300, 2 ml | Clear solution |
| PLGA (70:30), 0.2 g | PEG 200, 2 ml | Clear solution |
| PLGA (70:30), 0.1 g | DMA, 20 Drops | Clear solution |
| PLGA (85:15), 0.1 g | PEG 400, 1 ml | Partially soluble* |
| PLGA (50:50), 0.1 g | PEG 400, 1 ml | Partially soluble* |
| PLGA (85:15), 0.1 g | DMA, 1 ml | Clear solution |
| PLGA (50:50), 0.1 g | DMA, 1 ml | Clear solution |
| PLGA (90:10), 0.1 g | PEG 400, 2 ml | Partially soluble* |
| PLGA (70:30), 0.1 g | Cremophor EL, 2 ml | Partially soluble |
| PLGA (70:30), 0.1 g | Cremophor EL-P, 2 ml | Partially soluble |
| PLGA (70:30), 0.1 g | Benzyl alcohol, 0.5 ml | Clear solution |
| PLGA (70:30), 0.1 g | Benzyl benzoate, 0.5 ml | Miscible solution |

*PLGA (50:50), PLGA (85:15) and PLGA (90:10) were supplied in pellet form and were slow to dissolve in PEG solvent.

When the solutions were slowly injected into water containing 0.9% NaCl, the injected samples were observed to form gels. The rate of gelation depended on the identity of the solvent, the ratio of solvent to polymer, and the lactide/glycolate ratio of the polymer.

Example 2

Release Profiles for Morphine-Diclofenac Co-Drug from PLGA (70:30)/PEG Formulations Three formulations were evaluated to compare release profiles for morphine-diclofenac co-drug from different concentrations of PLGA (70:30): Formulation A was formulated at about 10 mg/ml morphine-diclofenac co-drug in PLGA (70:30)/PEG 400 solution (~5% (w/v) PLGA in PEG). Formulation B was formulated at about 10 mg/ml morphine-diclofenac co-drug in PLGA (70:30)/PEG 400 solution (~10% (w/v) PLGA in PEG). Formulation C was formulated at about 10 mg/ml morphine-diclofenac co-drug in PLGA (70:30)/PEG 400 solution (~20% (w/v) PLGA in PEG).

Each formulation was loaded into a 1-ml syringe, and 100 µl aliquot was injected into a tube containing 10 ml of 10% plasma in HA (hyaluronic acid) phosphate buffer, pH 7.4. The samples were placed in a water bath at 37° C. for release study. At each time point, the entire release medium was removed and replaced with 10 ml fresh buffer. The removed solution was analyzed for morphine, diclofenac and the co-drug contents by HPLC.

Figure 1:
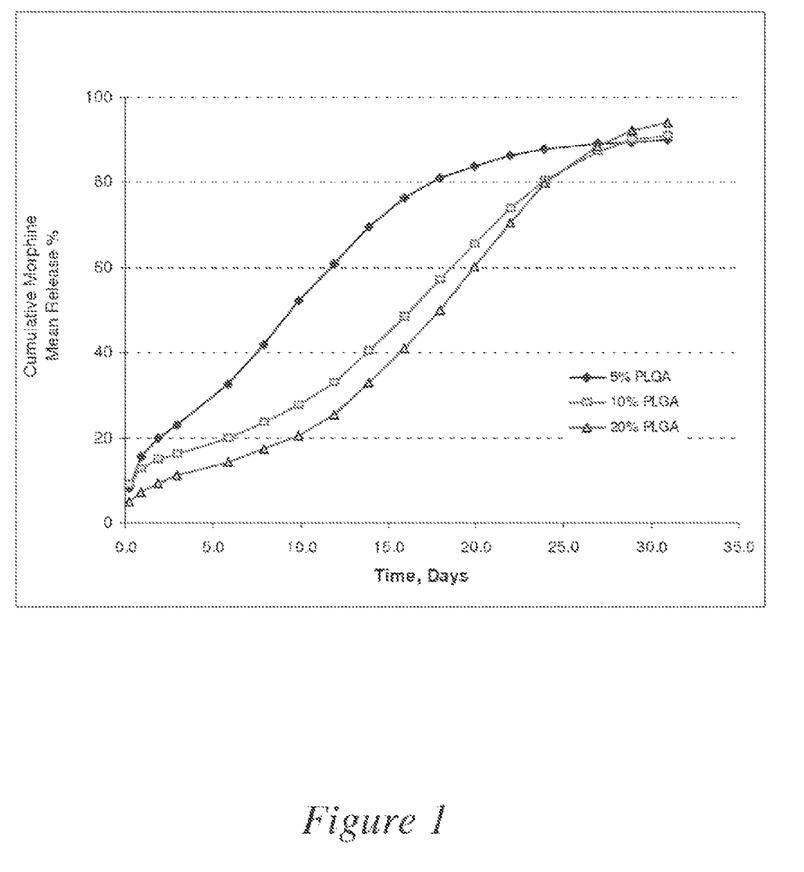
FIG. 1 shows the release profiles for morphine from three different morphine-diclofenac co-drug/PLGA (70:30)/PEG 400 formulations.

The results are shown graphically in FIG. 1. Morphine released much faster from the formulation A with 5% (w/v) PLGA. At day 18 about 80% morphine released. The release profiles of formulations B and C were very similar. At day 24 about 80% of the morphine was released from both formulations. However, the higher concentration of PLGA at 20% (w/v) reduced initial burst significantly.

No morphine-diclofenac co-drug was detected since the co-drug was hydrolyzed in the release medium. Diclofenac data (not shown) was not reliable, due to the high protein binding of diclofenac in the serum medium.

Example 3

Release Rate Profile for Morphine-Diclofenac Co-Drug from PLGA (50:50)/PEG Formulation The formulation was prepared with 12 mg/ml morphine-diclofenac co-drug in PLGA (50:50)/PEG 400 solution (~5% (w/v) PLGA in PEG) and loaded into a 1-ml syringe, and 100 µl aliquot was injected into a test tube containing 10 ml of 10% plasma in HA (hyaluronic acid) phosphate buffer, pH 7.4. The samples were placed in a 37° C. water bath. At each time point, the entire release medium was removed and replaced with 10 ml fresh buffer. The removed solutions were analyzed for morphine, diclofenac and the co-drug contents by HPLC.

Figure 2:
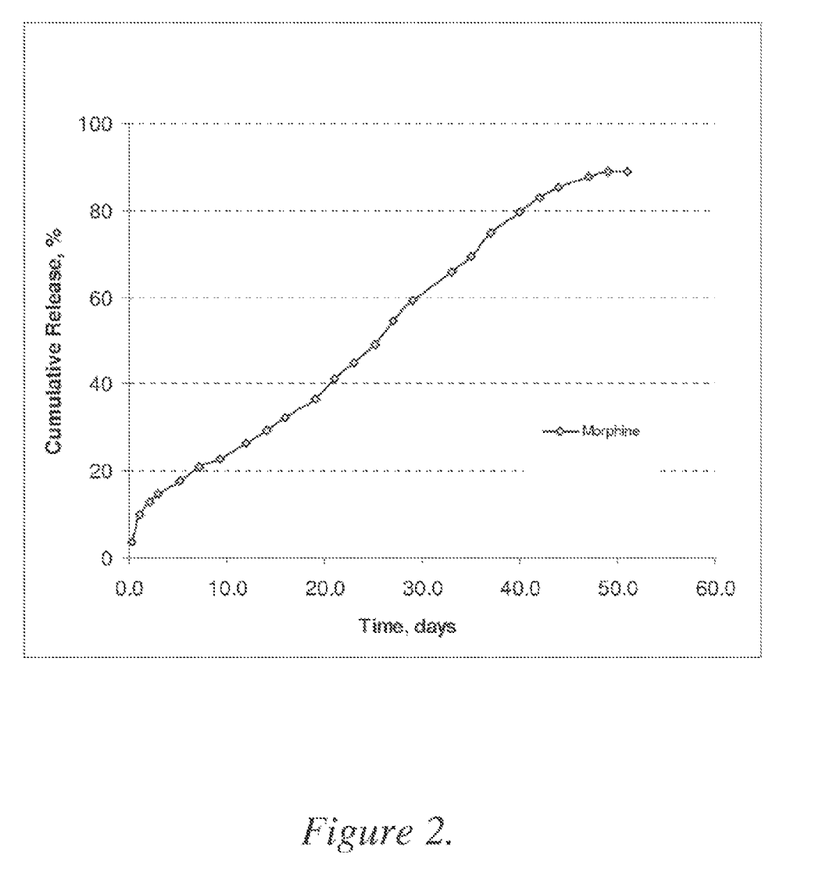
FIG. 2 shows the release profile for morphine from a morphine-diclofenac co-drug/PLGA (50:50)/PEG 400 formulation (5% w/y PLGA in PEG).

The results are shown graphically in FIG. 2. As compared to the results from Example 2, morphine release was much slower in this PLGA (50:50) formulation, even where the PLGA concentration was low as ~5% (w/v). About 80% of the morphine was released over 40 days. It is most likely that the higher molecular weight of PLGA (50:50) reduces the release rate of morphine.

Example 4

Release Profiles for Morphine-Diclofenac Co-Drug from PLGA (70:30) with Non-Polymeric Solvents Two formulations were evaluated for this study: Formulation A was formulated at about 8 mg/ml morphine-diclofenac co-drug in PLGA (70:30)/DMA solution (40% (w/v) PLGA in DMA). Formulation B was formulated at about 10 mg/ml morphine-diclofenac co-drug in PLGA (70:30)/benzyl benzoate solution (20% (w/v) PLGA in benzyl benzoate).

Each formulation was loaded into a 1-ml syringe, and 100 µl aliquot was injected into a tube containing 10 ml of 10% plasma in HA (hyaluronic acid) phosphate buffer, pH 7.4. The samples were placed in a water bath at 37° C. for release study. At each time point, the entire release medium for the DMA formulation was removed and replaced with 10 ml fresh buffer, while only 5 ml release medium for the benzyl benzoate formulation was removed and replaced with 5 ml fresh buffer. The removed solutions were analyzed for morphine, diclofenac and the co-drug contents by HPLC.

Figure 3:
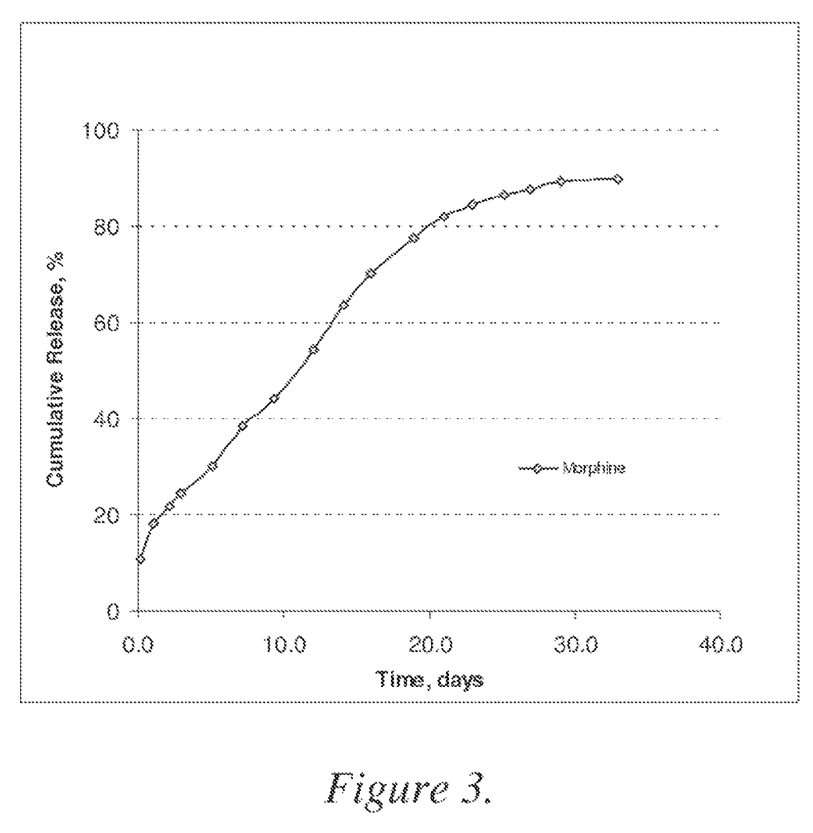
FIG. 3 shows the release profile for morphine from a morphine-diclofenac co-drug/PLGA (70:30)/DMA formulation.
Figure 4:
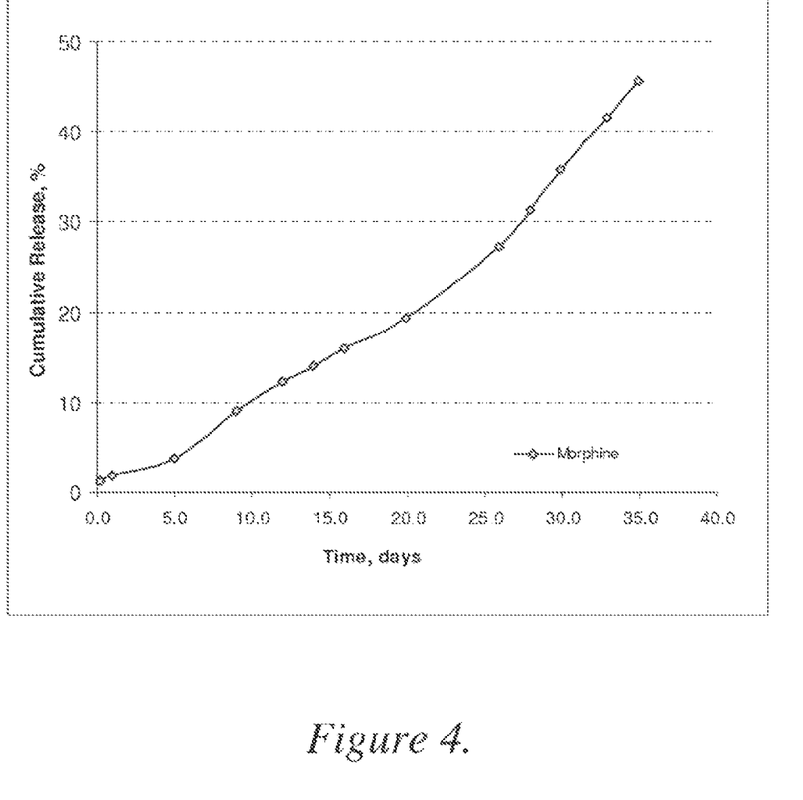
FIG. 4 shows the release profile for morphine from a morphine-diclofenac co-drug/PLGA (70:30)/benzyl benzoate formulation (20% w/v PLGA in benzyl benzoate).

The results are shown in FIGS. 3 (DMA) and 4 (benzyl benzoate). The morphine release profile from the DMA formulation is very similar to that from the formulation with 5% (w/v) PLGA in Example 2, although the concentration of PLGA in the DMA formulation was 40% (w/v). However, morphine release was slower in the benzyl benzoate formulation. At day 35 about 46% morphine was released. DMA is more hydrophilic than benzyl benzoate, which is an oily solvent. By adding these organic solvent(s) to PLGA formulations, drug release rate can be adjusted.

All references, publications, and patents cited herein are hereby incorporated by reference in their entirety. From the foregoing description, it will be apparent to one of ordinary skill in the art that, without departing from the spirit and scope thereof, various changes and/or modifications of the invention may be made to adapt it to particular usages and conditions. Such changes and/or modifications are contemplated to be within the full range of equivalence of the following claims.

We claim:

1. A method for forming a polymeric sustained-release drug delivery gel in a subject, comprising injecting into the subject a drug delivery device comprising a fluid composition, wherein:
    the device comprises a tube;
    the fluid composition is positioned in the tube;
    the fluid composition comprises a drug, a biocompatible and bioerodable poly(DL-lactide-glycolide) (PLGA) polymer, and a polyoxyethylene ether;
    the polyoxyethylene ether serves as a solvent for the PLGA polymer; and
    the composition forms a gel phase when said composition comes into contact with water or bodily fluids.

2. The method according to claim 1, wherein the composition is co-injected with an aqueous fluid.

3. The method according to claim 2, wherein the aqueous fluid is buffered saline.

4. The method according to claim 1, wherein the device has at least one opening.

5. The method according to claim 1, wherein the device is an open tube.

6. The method according to claim 1, wherein the polyoxyethylene ether is polyethylene glycol (PEG).

7. The method according to claim 6, wherein the average MW of the polyethylene glycol is between about 100 and about 6000.

8. The method according to claim 6, wherein the average MW of the polyethylene glycol is between about 200 and about 400.

9. The method according to claim 1, wherein the drug is a pegylated prodrug.

10. The method of claim 1, wherein the release rate of the drug from the device is dependent on the surface area of the composition that is exposed to water or bodily fluids.

* * * * *